United States Patent [19]

Dolphin et al.

[11] Patent Number: 5,308,608
[45] Date of Patent: May 3, 1994

[54] PHOTOSENSITIZING DIELS-ALDER PORPHYRIN DERIVATIVES

[75] Inventors: David Dolphin; Paul Y. Hin; Tilak Wijesekera, all of Vancouver, Canada

[73] Assignee: University of British Columbia, Vancouver, Canada

[21] Appl. No.: 940,673

[22] Filed: Sep. 4, 1992

Related U.S. Application Data

[60] Division of Ser. No. 633,137, Feb. 28, 1991, Pat. No. 5,149,708, which is a continuation-in-part of Ser. No. 363,185, Jun. 7, 1989, abandoned.

[51] Int. Cl.$^5$ .............................. A61K 31/40
[52] U.S. Cl. ........................... 424/9; 424/2; 424/7.1; 514/410
[58] Field of Search ............... 424/2, 7.1, 9; 514/410; 540/145

[56] References Cited

U.S. PATENT DOCUMENTS

| | | | |
|---|---|---|---|
| 4,268,947 | 5/1981 | Hile | 29/451 |
| 4,485,806 | 12/1984 | Akers | 128/1 |
| 4,500,507 | 2/1985 | Wong | 424/1.1 |
| 4,512,762 | 4/1985 | Spears | 604/21 |
| 4,577,636 | 3/1986 | Spears | 128/654 |
| 4,649,151 | 3/1987 | Dougherty et al. | 514/410 |
| 4,727,027 | 2/1988 | Wiesehahn et al. | 435/173 |
| 4,748,120 | 5/1988 | Wiesenhahn | 435/173 |
| 4,753,958 | 6/1988 | Weinsein et al. | 514/410 |

FOREIGN PATENT DOCUMENTS

| | | |
|---|---|---|
| 175617 | 3/1986 | European Pat. Off. |
| 276121 | 7/1988 | European Pat. Off. |

OTHER PUBLICATIONS

Cavaleiro et al., *Diels-Alder Reactions of Photoporphyrin Dimethyl Esters with Nitrosobenzenes: A Novel Degradation to Formyl Porphyrins*, J. Chem. Soc., Chem Commun. 776-77 (1985).

Diamond et al., *Photodynamic Therapy of Malignant Tumours*, The Lancet 1175-77 (Dec. 2, 1972).

Dougherty et al., *Photoradiation Therapy for the Treatment of Malignant Tumors*, 38 Cancer Res. 2628-35 (1978).

Dougherty et al., *Section 4: Photosensitizers*, Cancer: Principles and Practice of Oncology 1836-44 (DeVita Jr. et al. eds. 1982).

Dougherty et al., *Photoradiation Therapy of Human Tumors*, The Science of Photo Medicine 625-38 (Regan and Parish eds. 1982).

Dougherty et al., *Photoradiation Therapy-Clinical and Drug Advances*, 160 Adv. in Exp. Med. Biol. 3-13 (1983).

Dougherty et al., *Porphyrin Localization and Treatment of Tumors*, Proceedings of the Clayton Foundation International Symposium 301-14 (Doiron and Gomer eds. 1983).

Dougherty et al., *Photodynamic Therapy (PDT) of Malignant Tumors*, 2 Critical Reviews in Oncology/Hematology 83-116 (Davis ed. 1984).

(List continued on next page.)

*Primary Examiner*—Richard L. Raymond
*Attorney, Agent, or Firm*—Morrison & Foerster

[57] ABSTRACT

A group of hydro-dibenzoporphyrins prepared by di-Diels-Alder additions at the A and C rings of the appropriate divinyl porphyrins have absorption maxima in the range of 700-820 nanometers and are photosensitizing agents. These compounds are useful in treating disorders or conditions which are subject to hematoporphyrin derivative (HPD) treatment in the presence of light, or in treating biological materials generally to destroy unwanted targets such as viruses, cells and tissues. The use of the compounds of the invention permits irradiation with wavelengths other than those absorbed by blood. The compounds of the invention may also be conjugated to ligands specific for receptors or to specific immunoglobulins or fragments thereof to home to target tissues or cells for the radiation treatment. Use of these materials permits lower levels of photosensitizer to be used, thus preventing side reactions which might destroy normal tissues.

4 Claims, 5 Drawing Sheets

OTHER PUBLICATIONS

Flitsch, *Hydrogenated Porphyrin Derivatives: Hydroporphyrins,* 43 Advances in Heterocyclic Chemistry 73–126 (1988).

Gregorie, Jr. et al., *Hematoporphyrin-Derivative Fluorescence in Malignant Neoplasms,* 167 Ann. Surg. 820–28 (1968).

Mew et al., *Photoimmunotherapy: Treatment of Animal Tumors with Tumor-specific Monoclonal Antibody-hematoporphyrin Conjugates,* 130 J. of Immunol. 1473–77 (1983).

Mew et al., *Ability of Specific Monoclonal Antibodies and Conventional Antisera Conjugated to Hematoporphyrin to Label and Kill Selected Cell Lines Subsequent to Light Activation,* 45 Cancer Res. 4380–84 (1985).

Richter et al., *Preliminary Studies on a More Effective Phototoxic Agent Than Hematoporphyrin,* 79 J. Natl. Cancer Inst 1327–32 (1987).

Weishaupt et al., *Identification of Singlet Oxygen as the Cytotoxic Agent in Photoinactivation of a Murine Tumor,* 36 Cancer Res. 2326–29 (1976).

Callott et al., *Additions to Porphins Involving the Formation of New Carbon-Carbon Bonds,* Perkin Transactions I, J. of Chem. Soc. 1424–27 (1973).

PHOTOSENSITIZING DIELS-ALDER PORPHYRIN DERIVATIVES

This application is a division of Ser. No. 07/633,137 filed Feb. 28, 1991 now U.S. Pat. No. 5,149,708, which is a continuation-in-part of Ser. No. 07/363,185 filed Jun. 7, 1989, now abandoned.

FIELD OF THE INVENTION

The invention relates to the use of light absorbing compounds to mediate the destruction of unwanted cells or tissues or other undesirable materials by irradiation. Specifically, the invention relates to the use of Diels-Alder derivatives of porphyrin having absorption maxima in the range 700-820 nanometers to mediate the irradiation of materials to be destroyed, and to the use of these compounds conjugated to target-specific ligands, such as receptor-specific ligands, or immunoglobulins or their immunospecific fragments, to focus the effects of the irradiation on particular targets.

BACKGROUND OF THE INVENTION

The use of hematoporphyrin and its acetylated derivative mixture hematoporphyrin derivative (HPD) systemically, combined with irradiation, for the detection and treatment of malignant cells has, by this time, some considerable history. HPD is a mixture of porphyrins including hematoporphyrin itself, hydroxyethyl vinyl deutero porphyrin, protoporphyrin, and dihematoporphyrin ethers. (See, e.g., "Porphyrin Photosensitization", Kessel, D., et al., eds. (1983) Plenum Press.)

HPD seems "naturally" capable of localizing in malignant cells. When irradiated, it has two properties which make it useful. First, when irradiated with ultraviolet or visible light, it is capable of fluorescence, and thus is useful in diagnostic methods related to detection of malignancy (see, for example, Kessel, et al. (supra); Gregory, H. B., Jr., et al., Ann Surg (1968) 167:827-829). More pertinent to the present invention is the capacity of HPD, when irradiated with visible light, to exhibit a cytotoxic effect on the cells in which it is localized (see, for example, Diamond, I., et al., Lancet (1972) 2:1175-1177; Dougherty, T. J., et al., Cancer Research (1978) 38:2628-2635; Dougherty, T. J., et al., "The Science of Photo Medicine" (1982) J. D. Regan & J. A. Parrish, eds., pp. 625-638; Dougherty, T. J., et al., "Cancer: Principles and Practice of Oncology" (1982) V.T. DeVita Jr., et al., eds., pp. 1836-1844). Although it has not been definitively established, the effect of HPD in killing cells seems to be due to the formation of singlet oxygen upon irradiation (Weishaupt, K. R., et al., Cancer Research (1976) 36:2326-2329). Several mechanisms for this effect have been proposed, and it has recently been shown that the active ingredient in HPD which mediates the cytotoxic effect of visible light irradiation is the mixture of dihematoporphyrin ethers (DHE) (Dougherty, T. J., et al., "Porphyrin Localization and Treatment of Tumors" (1984) pp. 301-314; Dougherty, T. J., CRC Critical Reviews in Oncology/Hematology (1984) 2:83-116).

A purified form of the active component(s) of HPD is obtained by adjustment of pH to cause aggregation and recovery of the aggregate, as disclosed in U.S. Pat. No. 4,649,151. The purified form, called DHE in the patent, is marketed under the trademark Photofrin II and has been used in a manner completely analogous to HPD.

In addition to in vivo therapeutic and diagnostic protocols for tumors as described in the above-cited patent, the porphyrins, including HPD and its more purified derivatives, can be used in other in vivo and in vitro applications. For example, photosensitizers are useful in the detection and treatment of atherosclerotic plaques as described in U.S. Pat. Nos. 4,512,762 and 4,577,636. U.S. Pat. Nos. 4,500,507 and 4,485,806 describe the use of radiolabeled porphyrin compounds, including HPD, for tumor imaging. U.S. Pat. No. 4,753,958 to the University of California describes the use of topical application of porphyrin sensitizers for diagnosis and treatment of skin diseases. U.S. Pat. No. 4,748,120 describes the use of photosensitizers in the treatment of whole blood or blood components. Photochemical decontamination treatment of blood and components is also described in U.S. Pat. No. 4,727,027 where the photosensitizer is furocumarin and its derivatives. In addition, viruses are inactivated in therapeutic protein compositions in vitro as disclosed in U.S. Pat. No. 4,268,947.

While the treatment of tumors and other undesirable targets with HPD relies on the intrinsic ability of HPD to localize in malignant cells, a considerable improvement and refinement in specificity has been achieved by conjugating the hematoporphyrin to tumor-specific antibodies. For example, when hematoporphyrin was coupled to monoclonal antibodies directed to a murine myosarcoma cell line M1, administration of anti-M1 hematoporphyrin-conjugates to tumor-bearing animals followed by exposure to incandescent light resulted in the suppression of M1 growth (Mew, D., et al., J Immunol (1983) 130:1473-1477). In additional work, hematoporphyrin was conjugated to a monoclonal antibody specific to an antigen associated with a human leukemia (CAMAL) and the conjugates were shown to mediate the irradiation-induced killing of leukemic cells specifically, in vitro (Mew, D., et al., Cancer Research (1985) 45:4380-4386).

While the conjugation of hematoporphyrin to immunoglobulins specific for targeted cells refines the ability of the hematoporphyrin to home to the desired cells or tissue, this still does not solve another problem ancillary to this general therapeutic approach, namely that the wavelength for irradiation required to activate the hematoporphyrin or HPD, which is in the range of 630 nanometers, is also an energy which is readily absorbed by the porphyrins and other natural chromophores in the blood and other tissues. Therefore, relatively large amounts of the hematoporphyrin or HPD must be administered, often resulting in oversensitization of the patient to light in general. It would be desirable to administer compounds to mediate the effects of irradiation in a lower amount, thus avoiding the problems of hypersensitivity exhibited nonspecifically throughout the subject organism. The ability to use light not absorbed by the tissue constituents also permits increased depth of light penetration.

A class of compounds which have been designated hydro-monobenzoporphyrins and their derivatives (BPD) are disclosed in the above cross-referenced applications and the activity of certain of BPD compounds was described in a paper by Richter, A. M., et al., in J Natl Cancer Inst (1987) 79:1327-1332, incorporated herein by reference. These compounds absorb light in the range of 670-780 nm and are useful in a manner similar to HPD. The compounds of the present invention which are di-Diels-Alder adducts of dienophiles to diagonal rings in the porphyrin system add to the repertoire of useful photosensitizers which have absorption maxima in the noninterfering range of 700-820 nm, which permit reduced dosage and enhanced light penetration.

The attempted preparation of di-Diels-Alder adducts to the A and C rings of protoporphyrin II was reported by Cavaleiro, J. A. S., et al., *J Chem Soc Chem Commun* (1985) 776-777. In this report, protoporphyrin II was reacted with a nitrosobenzene derivative as a dienophile and resulted in the formation of unstable products which could not be isolated. A secondary report of this same work was also given by Flitsch, W., in *Advances in Heterocyclic Chemistry* (1988) 43:104-105.

DISCLOSURE OF THE INVENTION

The invention provides light absorbing compounds capable of exhibiting light-mediated cytotoxic and diagnostic effects. In addition to their in vitro use, these compounds may be administered in in vivo relatively low dosage due to their capability to absorb radiation whose energy range is outside of that normally absorbed by the components present in high concentration in the blood or other tissues, in particular, the porphyrin residues normally associated with hemoglobin and myoglobin. Therefore, by providing these modified porphyrins for in vivo treatment at lower concentration, hypersensitivity of nontarget tissues is reduced, and the irradiation treatment can be conducted at a wavelength at which the native chromophores do not compete for photons with the active compounds, resulting in greater depth of penetration of the light. Similar advantages accrue in in vitro treatment of colored materials, such as blood samples.

These photoactive compounds are modified porphyrins which, by virtue of their derivatization, undergo a shift in absorption maxima so that they appear green rather than red, indicating their absorption of wavelengths in the red-orange range. They confer sensitivity on target cells at concentrations greater than 10-fold lower than those required for hematoporphyrin (Hp) or HPD.

The compounds of the invention are derived from protoporphyrin II and other A/C divinyl analogs—i.e., analogs corresponding to modifications of protoporphyrin IX which contain vinyl substituents in the A and C rather than the A and B rings, which are tautomers of the B/D divinyl porphyrins that lead to the same Diels-Alder products. It is understood that for symmetrically substituted prophyrins, such as those illustrated herein, the A/C and B/D divinyls are actually exactly equivalent; however, when substitution on the ring system is not symmetrical, the forms are tautomeric. However, since the same Diels-Alder products result, the compounds of the invention will be referred to as A/C derivatives.

The compounds of the invention are obtained by Diels-Alder reactions with both of the vinyl groups, resulting in fused six-membered rings attached both to the A and C rings. The resulting derivatives are of the same oxidation state as bacteriochlorin (or bacteriochlorophyll). Because of their structural derivation, they have been designated herein A/C hydro-dibenzoporphyrin compounds as is further explained below.

Thus, A/C hydro-dibenzoporphyrin compounds of the invention are selected from a group of derivatives obtained using Diels-Alder reactions of ethylene or acetylene dienophiles with protoporphyrin II, or other A/C divinyl porphyrins under conditions which effect a reaction at both available conjugated, nonaromatic diene structures present in the relevant porphyrin ring system (rings A and C). The formulas shown in FIG. 1 represent the A/C hydro-dibenzo porphyrins of the invention.

The modified A/C hydro-dibenzo-porphyrins of the invention can be used per se or can be conjugated to specific ligands reactive with a target, such as receptor-specific ligands or immunoglobulins or immunospecific portions of immunoglobulins, permitting them to be more concentrated in a desired target tissue or substances. This conjugation permits further lowering of the required dose levels since the material is not wasted in distribution into other tissues whose destruction, far from being desired, must be avoided.

In one aspect, the invention relates to a compound of the formulas 1-1 through 1-6 in FIG. 1, which compound is fluorescent and photosensitizing,
wherein at least one of $R^1$ and $R^2$ is selected from the group consisting of carbalkoxy (2-6C); aryl (6-10C); alkyl (1-6C) or aryl (6-10C) sulfonyl; cyano; and —$CONR^5CO$—, wherein $R^5$ is aryl (6-10C) or alkyl (1-6C); and the other $R^1$ and $R^2$ is selected from the group consisting of the aforesaid substituents and H; and wherein each $R^3$ and $R^4$ is independently selected from the group consisting of substituted or unsubstituted alkyl (1-6C); and substituted or unsubstituted omega-carboxyalkyl (2-6C) and the esters, amides, and salts thereof.

The invention also relates to labeled forms of these compounds.

In another aspect, the invention is directed to methods of locating or effecting cytotoxicity, i.e., photosensitizing, with respect to target materials using the A/C hydro-dibenzoporphyrins of the invention either alone or as conjugates. These A/C hydrodibenzoporphyrins are localized specifically in vivo to certain target tissues, where their presence can be detected by fluorescence, or by other means when the invention compounds are provided with additional or alternate labeling. As indicated above, the specificity of the compounds can be further enhanced by conjugation to ligands specific for the target. In addition, when the compounds are irradiated in situ using light in the range of 700-820 nm, photo activation results in cytotoxicity to the surrounding tissue. Cells to which the A/C hydrodibenzoporphyrin is normally attracted include tumor cells, and heoplastic cells in general, as well as bacteria and other diseased tissues. The method can be applied either in vitro or in vivo, and, when applied in vivo, can be topical or systemic.

In other aspects, the invention relates to conjugates of the formulas Re*-L-A/C and IG-L-A/C wherein Re* represents a ligand which is specific to, and capable of, binding a receptor at a cell surface, Ig represents an immunoglobulin or an immunologically reactive portion thereof, A/C represents a compound of the invention as defined above having an absorption maximum in the range of 700-820 nanometers, and L represents either a covalent bond linking these components or a linking moiety covalently linked to each of the Re* or Ig and invention compound.

The invention is also directed to tripartite complexes which include Re*-L-A/C or Ig-L-A/C; further conjugated to or associated with a label. The label may be bound either to the targeting component or to the A/C or both.

In another aspect, the invention relates to pharmaceutical compositions containing these active ingredients.

MODES OF CARRYING OUT THE INVENTION

The A/C Adducts

All of the compositions of the invention employ, as the light absorbing moiety, one or more derivatives of the protoporphyrin ring system which has a light absorption maximum in the range of 700–820 nanometers. FIGS. 2A–2D show the absorption spectra of some of the compounds of the invention shown in FIG. 1; all have absorptions close to 800 nm.

In general, this shift is achieved by effectively saturating one of the two π-bonds in two of the four pyrrole rings which constitute the typical porphyrin system. In protoporphyrin-II, two of the diagonally positioned pyrroles (A and C or B and D which are, in this case, equivalent,) contain vinyl substitutions such that the exocyclic π-bond is conjugated to one of the two π-bonds in the ring. These vinyl substituents are coupled to positions 2,12 (or 1,5 if only the perimeter positions are numbered).

Figure 1:
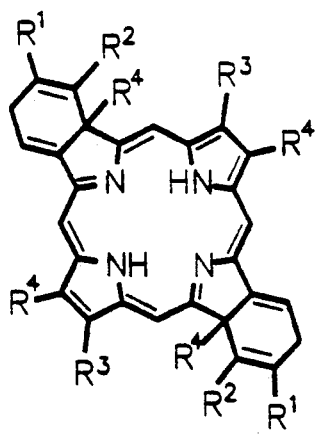
FIGS. 1-1–1-6 shows the structures of A/C compounds of the invention.
Figures 1, 2:
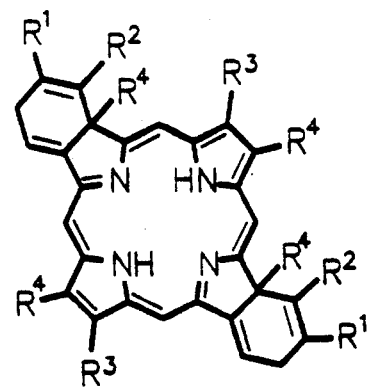
Figures 1, 2, 3:
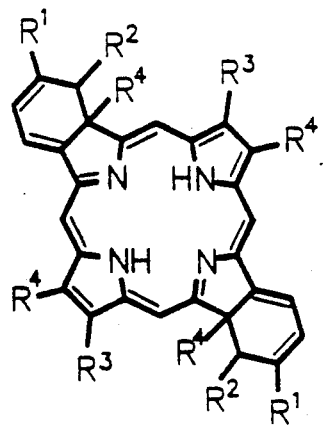
Figures 1, 2, 3, 4:
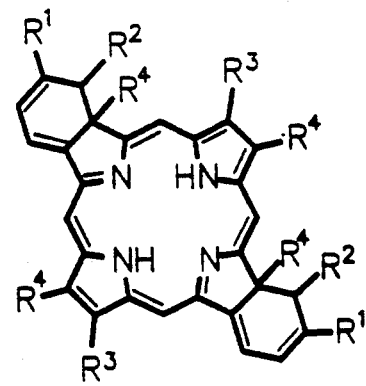
Figures 1, 2, 3, 4, 5:
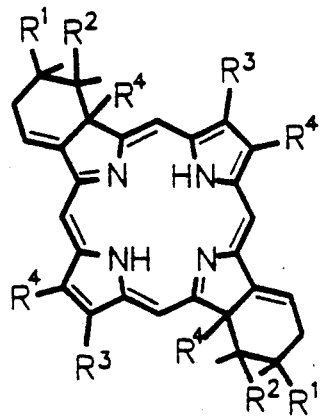
Figures 1, 2, 3, 4, 5, 6:
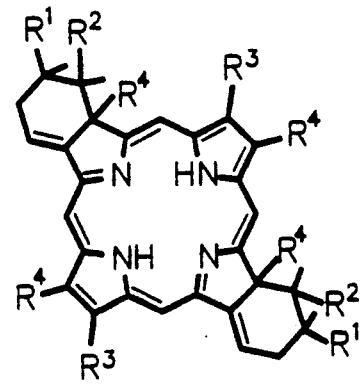

A Diels-Alder reaction involving these conjugated systems with an ethylene or acetylene dienophile results in six-membered rings fused to the A and C rings. The resultant of this addition is shown in FIG. 1 as formula 1-1 (for addition of acetylene dienophiles) and as formula 1-5 (for addition of ethylene dienophiles). Rearrangement of the π system in the hexadiene ring obtained in formula 1-1 results, as shown, in the compound of formula 1-3; reduction provides an alternative route to the compounds of formula 1-5. As stated above, compounds of the formula 1-5 can be provided directly by reaction of the protoporphyrin system with an ethylene dienophile. All of these compounds provide the desired shift in absorption maximum. The corresponding adducts starting with the porphyrin ring system in which the A/C rings contain vinyl substituents at positions numbered 2,13 (or 1,6) are shown as formulas 1-2, 1-4 and 1-6.

Reaction of protoporphyrin II or other A/C or B/D divinyl analogs with, for example, diethyl acetylene dicarboxylate (DEAD)—results in the compounds shown as formulas 1-1 and 1-2 of FIG. 1, wherein $R^1$ and $R^2$ rep resent the substituents on the original acetylene-derived Diels-Alder reagent, $R^1C \equiv CR^2$, in this case, carboethoxy.

The name "hydro"-dibenzoporphyrin is used for convenience herein and includes the compounds shown as 1-1 through 1-6 in FIG. 1. Thus this term refers to the direct and rearrangement products of the Diels-Alder reaction of the porphyrin ring system with $R^1C \equiv C-R^2$ and also refers to the reduced products of formulas 1-5 and 1-6. Hydro-dibenzoporphyrin is used generically to include both indicated oxidation states.

Analogs containing the exocyclic "benzo" rings completely reduced are not included in the invention and are not included in this term as used herein. The dibenzoporphyrins per se are also outside the scope of the invention as their absorption maxima do not fall within the required range. Thus, A/C (2,12) hydrodibenzo porphyrin refers generically to compounds of formulas 1-1, 1-3 and 1-5; A/C (2,13) hydro-dibenzoporphyrin refers generically to compounds of formulas 1-2, 1-4 and 1-6.

In general, $R^1$ and $R^2$ are each, independently, electron-withdrawing substituents, and are, most commonly, carbalkoxy (2-6C); aryl (6-10C); alkyl (1-6C) or aryl (6-10C) sulfonyl; —CONR$^5$CO-wherein $R^5$ is aryl (6-10C) or alkyl (1-6C); cyano; or any other activating substituents. One of $R^1$ and $R^2$ may optionally be H while the other is an electron withdrawing substituent as set forth above of sufficient strength to facilitate the Diels-Alder reaction. $R^1$ and $R^2$ are preferably carbalkoxy groups such as carboethoxy.

As used herein, carboxy is, as conventionally defined, —COOH, and carbalkoxy is —COOR, wherein R is alkyl (1-6C). As used herein, alkyl (1-6C) is a saturated straight or branched chain hydrocarbon of 1–6 carbon atoms such as methyl, ethyl n-hexyl, 2-methylpentyl, t-butyl, n-propyl, and so forth.

Aryl (6-10C) is phenyl optionally substituted with 1–3 substituents independently selected from halo (fluoro, chloro, bromo or iodo), lower alkyl (1-4C) or lower alkoxy (1-4C). (Alkoxy is —OR wherein R is alkyl as herein defined.)

The aryl (6-10C) or alkyl (1-6C) sulfonyl moieties have the formula SO$_2$R wherein R is alkyl or is aryl as above-defined.

$R^3$ and $R^4$ represent substituents present on the porphyrin used in the reaction or substituents derived therefrom. In protoporphyrin-II, all $R^4$ are methyl and both $R^3$ are 2-carboxyethyl (—CH$_2$CH$_2$COOH) and the vinyl groups are positioned 2,12. However, the natures of $R^3$ and $R^4$ (unless they contain π-bonds conjugated to ring π-bond), are ordinarily not relevant to the progress of the Diels-Alder reaction (although it should be noted that while they do not ordinarily influence the course of the Diels-Alder reaction by altering the nature of the diene substrate, their influence on other factors, such as suitable solubility characteristics, lack of interference with the progress of the reaction, and effectiveness and absorption spectrum of the resulting product, are relevant). In the invention compounds, $R^3$ and $R^4$ are substituted or unsubstituted alkyl (1-6C), or substituted or unsubstituted 1-carboxyalkyl (2-6C) or the esters, amides or salts thereof. The substituents may include, for example, halogen as above-defined, and/or other nonreactive substituents. Alkyl is as above defined. Omega carboxyalkyl (2-6C) refers to substituents of the formula —(CH$_2$)$_n$COOH wherein n is 1–5.

The invention compounds also include the salts, esters and amides of —COOH. For use in vivo these salts, esters and amides must be pharmaceutically acceptable and nontoxic; this requirement is not germane to in vitro use.

"Salts, esters, and amides" refers to salts derived from inorganic or organic bases, including pharmaceutically acceptable nontoxic inorganic and organic bases, and alkyl esters or amides derived from alcohols or primary or secondary amines of the formula ROH or RNH$_2$ or R$_2$NH wherein R is alkyl as herein defined.

Suitable inorganic bases include sodium, potassium, lithium, ammonium, calcium, and magnesium, hydroxides, and the like. Particularly preferred are the potassium and sodium salts. Pharmaceutically acceptable organic nontoxic bases include primary, secondary, tertiary and quaternary amines including cyclic amines, and basic ion-exchange resins. Examples include isopropylamine, trimethylamine, ethanolamine, dicyclohexylamine, lysine, arginine, histidine, caffeine, procaine, choline, betaine, glucosamine, theobromine, purines, piperazine, piperidine, polyamine resins, and the like.

The salt derivatives are prepared by treating the free acids with an appropriate amount of pharmaceutically acceptable base. The reaction is conducted in water, alone or in combination with an inert, water-miscible organic solvent, at a temperature of from about 0° C. to about 100° C., preferably at room temperature at a suitable molar ratio of invention compound to base. Typical inert, water-miscible organic solvents include methanol, ethanol, isopropanol, butanol, acetone, dioxane or tetrahydrofuran.

The salt derivatives can be reconverted to their respective free acids by acidifying with an acid, preferably an inorganic acid, e.g., hydrochloric acid, sulfuric acid and the like, at a temperature of from about 0° C. to about 50° C., preferably at room temperature.

The esters are prepared by esterifying the corresponding free acids with an alcohol reagent corresponding to the desired ester. This reaction is conducted in the presence of a strong acid, such as boron trifluoride, hydrogen chloride, sulfuric acid, p-toluenesulfonic acid, and the like. Since the alcohol reagent used in the esterificaion is a liquid at the reaction temperature, the alcohol reagent can be the reaction solvent. optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichlorethane; or an ether solvent, e.g., diethyl ether, dibutyl ether, dioxane, tetrahydrofuran, and the like. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic colvent, such as diethyl ether, benzene, methylene chloride, and the like, combining the extracts, washing the extracts with water to neutrality, and then evaporating under reduced pressure.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by transesterification to the ethyl ester.

In still another alternative, the ester can be prepared by reacting the free acid form with the appropriate diazo alkane, such as diazomethane, diazo-n-hexane, or diazo-i-propane in an aprotic organic solvent at low temperature.

The amides are obtained by activation of the carboxylic acid residue and treating with the appropriate amine.

Preparation Methods

Since the compounds of the invention are seen as related to compounds with substituents corresponding to those naturally occurring in porphyrins, among the preferred embodiments of $R^3$ are $CH_2CH_2COOH$ or the esters, amides or salts thereof, and a preferred embodiment of $R^4$ is methyl. However, all of the divinyl porphyrin nuclei used as the starting materials wherein the vinyl groups are positioned 2,12 can be prepared synthetically by methods known in the art, such as those shown in Reactions Schemes 1-3 to follow:

Schemes 1 and 2 show the method of Johnson as described by Paine, J. B., in "The Porphyrins", D. Dolphin, Ed., (1978) Vol. 1, J. Wiley & Sons, as applied to illustrations wherein all $R^4$ are methyl and $R^3$ are either alkyl or 1-carboxyalkyl. These methods involve reductive condensation of dipyrrole nuclei and dehydration of alcohol to obtain the vinyl substituents. Scheme 3 shows an alternate method also described in "The Porphyrins" (supra) which employs symmetric condensation of individual pyrroles and debromination. A different method uses the condensation of dipyrromethane with b-bilene, as described by Clezy, P. S., et al., Aust J Chem (1980) 33:557; ibid. (1974)27:371.

To prepare the corresponding 2,13 divinyl porphyrin nuclei, asymmetric forms are employed in the condensation of the two halves of the ring system; thus

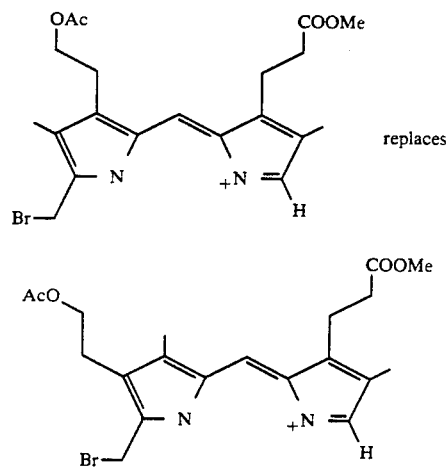

in Scheme 1 and a similar replacement is analogously made in Scheme 2. In Scheme 3,

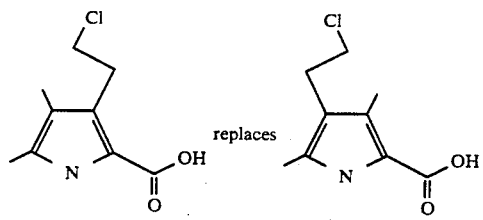

The starting porphyrin A/C divinyl compounds are then converted to the invention compounds by di Diels-Alder reactions. As shown in FIG. 1, the adducts formed by the reaction of $R^1-C\equiv C-R^2$ with the protoporphyrin ring system under conditions suitable for Diels-Alder reactions, as are known in the art, are compounds of the formulas 1-1 and 1-2 wherein the compound in formula 1-1 results from addition to divinyl substituents in the 2,12 positions and formula 1-2 results from addition to divinyl substituents in the 2,13 positions.

Scheme 1
Synthesis of Protoporphyrin II Via Johnson's Approach (Method I)
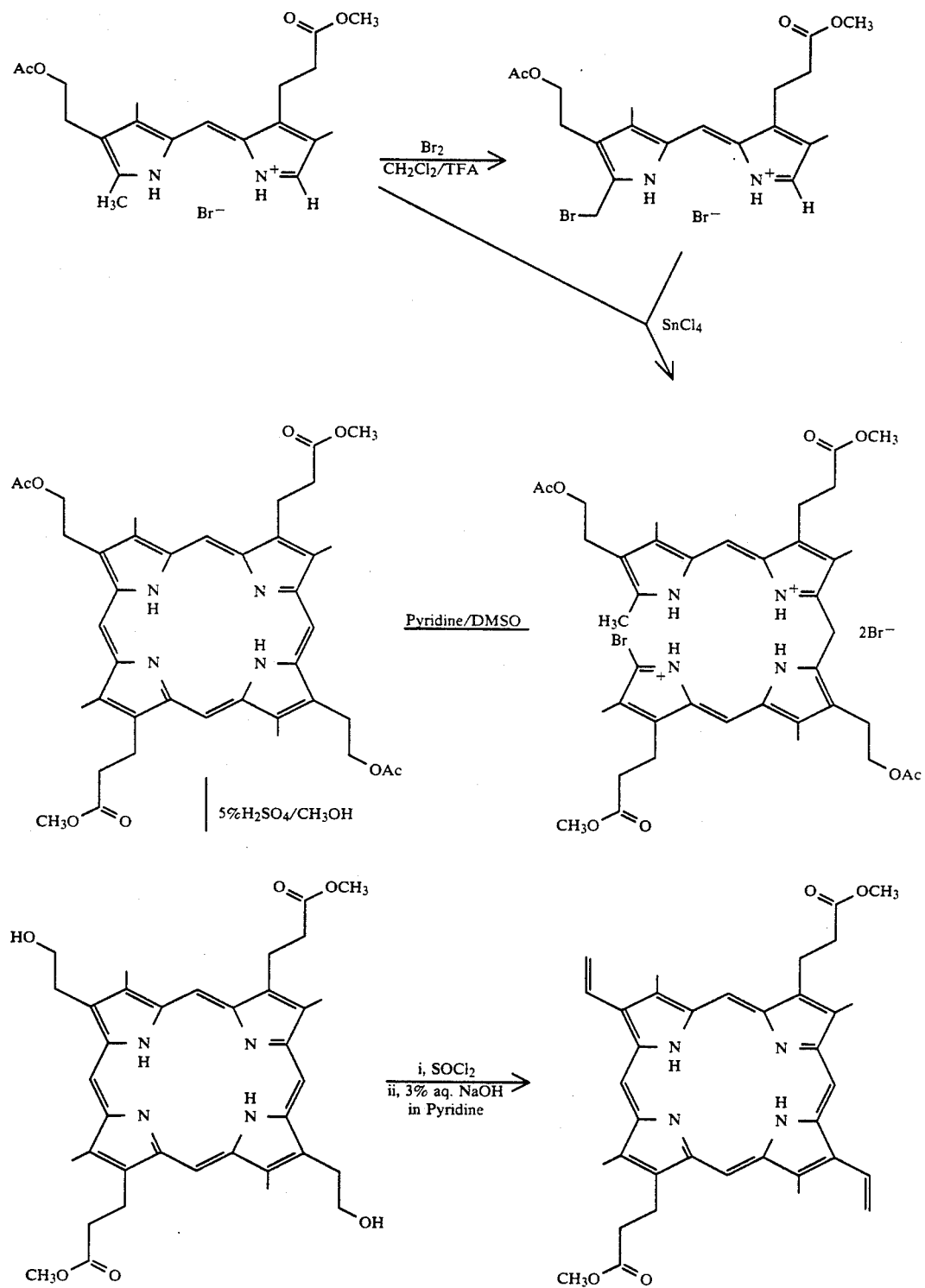

Scheme 2
Synthesis of A,C-Divinylporphyrin Via Johnson's Approach
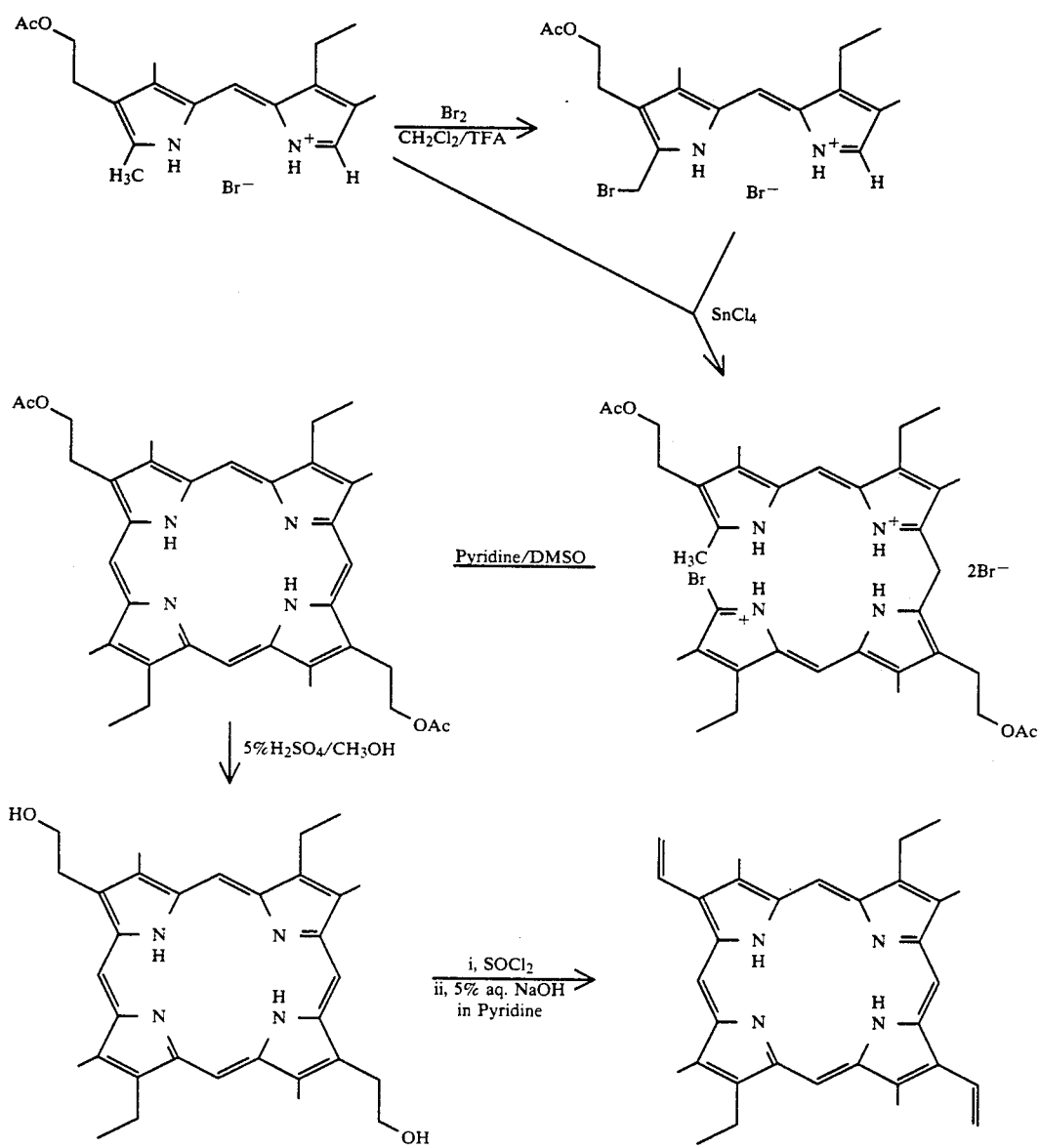
Scheme 3
Synthesis of Protoporphyrin II (Method 2)
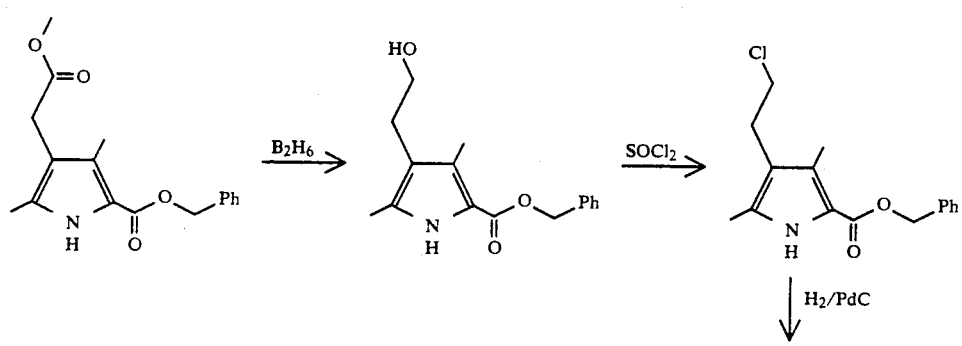

-continued
Scheme 3
Synthesis of Protoporphyrin II (Method 2)

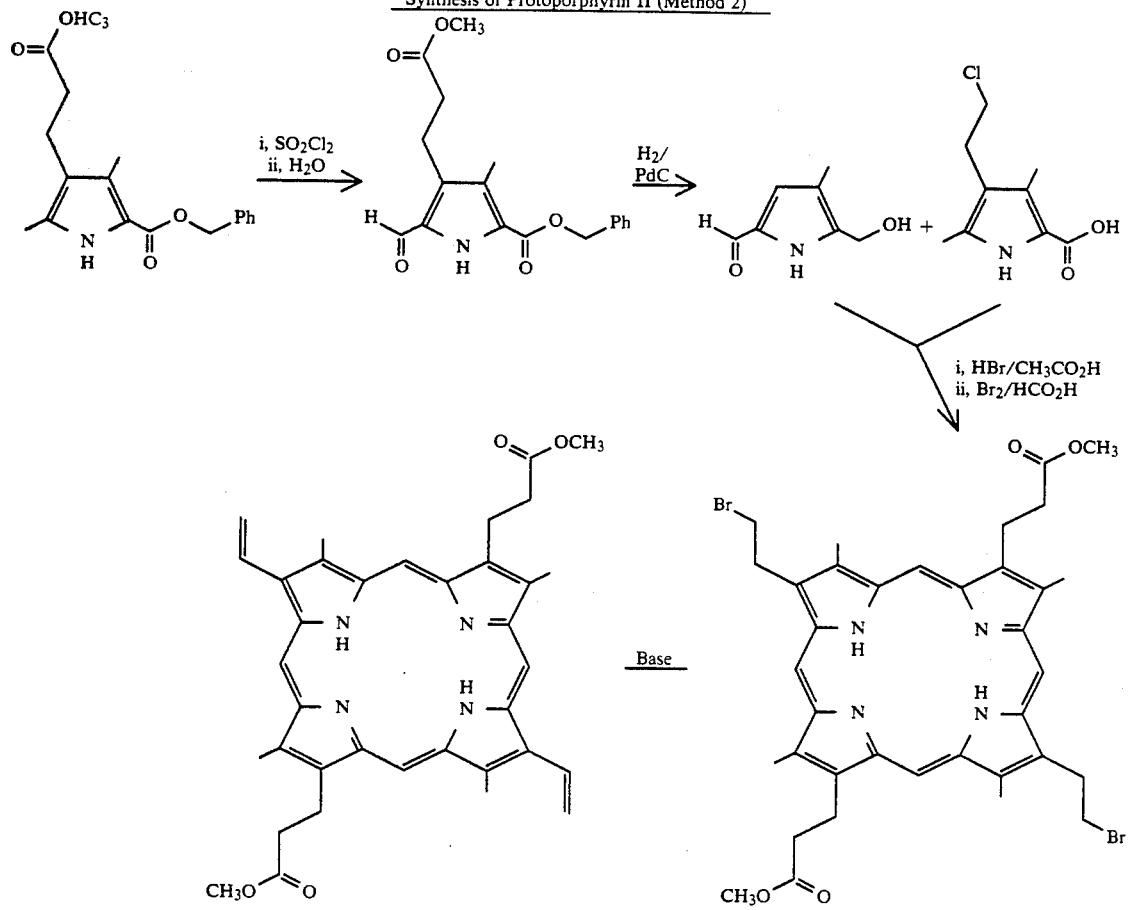

These compounds have absorption maxima in the 720–750 nm range.

These hydro-dibenzoporphyrins which directly result from the Diels-Alder reaction can also be isomerized in a manner as described for the corresponding hydro-monobenzoporphyrins by Morgan et al., *J Chem Soc Chem Commun* (1984) pp. 1047–1048; and Pangka et al., *J Org Chem* (1986) 51:1094, both incorporated herein by reference, to compounds of formulas shown as 1-3 and 1-4 of FIG. 1. Rearrangement is by treatment with suitable reagents such as triethylamine (TEA) in methylene chloride or 1,8-diaza bicyclo[5.4.0] undec-6-ene (DBU). The stereochemistry of the product is determined by the choice of reagent.

The depictions of compounds 1-3 and 1-4 in FIG. 1 do not show the relative position of the exocyclic $R^4$ group with respect to the $R^2$ substituent. It has been found by the authors cited above that rearrangement using TEA gives SiA geometry for the angular $R^4$ group and $R^2$, while treatment with DBU results in the trans product. The cis product is evidently kinetically controlled since treatment of the cis product with DBU results in a further rearrangement to trans stereochemistry. Thus, formulas 1-3 and 1-4 of FIG. 1 show the rearranged products generically, from either TEA or DBU catalyzed rearrangement. The compounds of formulas 1-3 and 1-4 absorb in the 770–820 nm range.

In addition, the Diels-Alder products can be selectively reduced by treating with hydrogen in the presence of palladium on charcoal to give the saturated ring analogs, shown as formulas 1-5 and 1-6 in FIG. 1, corresponding to the respective Diels-Alder products of rings A and C and B and D. These reduced products also absorb light at 720–750 nm and are less preferred in the method of the invention than the compounds of formulas 1-3 and 1-4.

The compounds of formulas 1-5 and 1-6 may also be prepared directly by reaction of the appropriate divinyl porphyrin starting materials with an ethylene dienophile. Thus, they are formed by reaction of the appropriate porphyrin with a compound of the formula $R^1CH=CHR^2$ wherein $R^1$ and $R^2$ are as above defined.

It will be noted that many of the compounds of FIG. 1 contain at least one chiral center and therefore exist as optical isomers. The conjugates and methods of the invention include compounds having both configurations of the chiral carbons, whether the compounds are supplied as isolates of a single stereoisomer or are mixtures of enantiomers and/or diasteriomers. Separation of mixtures of diasteriomers may be effected by any conventional means; mixtures of enantiomers may be separated by usual techniques of reacting them with optically active preparations and separating the resulting diasteriomers.

It should further be noted that the compounds of the invention may be used as separated forms—i.e., for example, formula 1-3 alone or 1-4 alone, or mixtures in any ratio may be employed in the methods of therapy and diagnosis set forth herein.

The Target-Specific Component

The target-specific component can be, for example, an immunoglobulin or portion thereof or a ligand specific for receptor.

The immunoglobulin component can be any of a variety of materials. It may be derived from polyclonal or monoclonal antibody preparations and may contain whole antibodies or immunologically reactive fragments of these antibodies such as F(ab')$_2$, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Mono clonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L, supra.

Particularly useful antibodies exemplified herein include the monoclonal antibody preparation CAMAL-1 which can be prepared as described by Malcolm, A., et al., *Ex Hematol* (1984) 12:539-547; polyclonal or monoclonal preparations of anti-M1 antibody as described by Mew, D., et al., *J Immunol* (1983) 130:1473-1477 (supra) and B16G antibody which is prepared as described by Maier, T., et al., *J Immunol* (1983) 131:1843; Steele, J. K., et al., *Cell Immunol* (1984) 90:303, all incorporated herein by reference.

The foregoing list is exemplary and certainly not limiting; once the target tissue is known, antibody specific for this tissue may be prepared by conventional means. Therefore the invention is applicable to effecting toxicity against any desired target.

The ligand specific for receptor, Re*, refers to a moiety which binds a receptor at cell surfaces, and thus contains contours and charge patterns which are complementary to those of the receptor. The ligand specific for receptor is symbolized in the formulas of the compounds of the invention as Re*, wherein the asterisk indicates that the moiety bound in the compound of the invention is not the receptor itself, but a substance complementary to it. It is well understood that a wide variety of cell types have specific receptors designed to bind hormones, growth factors, or neurotransmitters. However, while these embodiments of ligands specific for receptor are known and understood, the phrase "ligand specific for receptor," as used herein, refers to any substance, natural or synthetic, which binds specifically to a receptor.

Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmit ters, such as acetylcholine, serotonin, and dopamine. Any analog of these substances which succeeds in binding to the receptor is also included.

Linkage

The conjugation of the target-cell-specific component to the hydro-dibenzoporphyrins can be effected by any convenient means. For proteins, such as Ig and certain Re*, a direct covalent bond between these moieties may be effected, for example, using a dehydrating agent such as a carbodiimide, in which case L represents a covalent bond. A particularly preferred method of covalently binding hydro-dibenzoporphyrins to the immunoglobulin moiety is treatment with I-ethyl-3-(3-dimethylamino propyl) carbodiimide (EDCI) in the presence of a reaction medium consisting essentially of dimethyl sulfoxide (DMSO).

Of course, other dehydrating agents such as dicyclohexylcarbodiimide or diethylcarbodiimide could also be used as well as conventional aqueous and partially aqueous media.

Nonprotein receptor ligands can be conjugated to the invention compounds according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Company, Rockford, Ill. These linkers are either homo or heterobifunctional moieties and include functionalities capable of forming disulfides, amides, hydrazones, and a wide variety of other linkages.

The most popular of these is N-succidimidyl-3-(2-pyridyldithio) propionate (SPDP). This reagent creates a disulfide linkage between itself and a cysteine residue in one protein and an amide link age through the e amino on a lysine or other free amino group in the other. A variety of such disulfide/amide-forming agents are known. See, for example, *Immun Rev* (1982) 62:185. Other bifunctional coupling agents form a thioether rather than a disulfide linkage. Many of these thioether-forming agents are commercially available and include reactive esters of 6-maleimidocaproic acid, 2-bromoacetic acid, 2-iodoacetic acid, 4-(N-maleimido-methyl) cyclohexane-1-carboxylic acid, and the like. The carboxyl groups can be activated by combining them with succinimide or 1-hydroxy-2-nitro-4-sulfonic acid sodium salt. A particularly preferred coupling agent is succinimidyl 4-(N-maleimido-methyl) cyclohexane-1-carboxylate (SMCC).

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

Label

For use in the method of the invention either the invention compounds per se or the conjugates may be further derivatized to a compound or ion which labels the drug. A wide variety of labeling moieties can be used, including radioisotopes, chromophores, and fluorescent labels. Radioisotope labeling is preferred, as it can be readily detected in vivo.

The compounds which are the invention hydrodibenzoporphyrins alone or which are conjugates of these with a specific binding substance can be labeled with radioisotopes by coordination of a suitable radioactive cation in the porphyrin system. Useful cations include technetium, gallium, and indium. In the conjugates, either or both the specific binding substances can be linked to or associated with label, or the label can be conjugated or coordinated with the hydro-dibenzoporphyrin moiety itself.

Metal Ions

The compounds of the invention can be administered or used in in vitro methods as shown above or when complexed to appropriate metal ions. As is generally understood in the art, the A/C hydro-dibenzo porphyrin nucleus can be treated with an appropriate ion such as magnesium ion, zinc ion, stannous ion, and the like to obtain the metal complex. As stated above, the metal ion may also be a radiolabel. The nature and desirability of the inclusion of a metal ion in the A/C hydro-dibenzoporphyrin nucleus depends on the specific application for which the compound is intended. When the inclusion of a metal ion is desired, the desired metal ion can be inserted using the appropriate metal salts under known conditions. For example, zinc ion can be introduced by treating the compound with zinc acetate in 1:1 methylene chloride:methanol.

Administration and Use

The improved photosensitizing compounds of the invention are thus useful in general, in the manner known in the art for hematoporphyrin derivative and for DHE. These materials are useful in sensitizing neoplastic cells or other abnormal tissue to destruction by irradiation using visible light—upon photoactivation, the compounds have no direct effect, nor are they entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluorescence which fluoresce can aid in localizing the tumor.

Typical indications, known in the art, include destruction of tumor tissue in solid tumors, dissolution of plaques in blood vessels (see, e.g., U.S. Pat. No. 4,512,762); treatment of topical conditions such as acne, athletes foot, warts, papilloma, and psoriasis and treatment of biological products (such as blood for transfusion) for infectious agents, since the presence of a membrane in such agents promotes the accumulation of the drug.

The conjugates of the invention, or the hydrodibenzoporphyrins when employed alone are formulated into pharmaceutical compositions for administration to the subject or applied to an in vitro target using techniques known in the art generally. A summary of such pharmaceutical compositions may be found, for example, in *Remington's Pharmaceutical Sciences*, Mack Publishing Co., Easton, Pa., latest edition.

The conjugates or compounds of the invention taken alone can be used in the systemic treatment of tumors and neoplastics made as bronchial, cervical, esophageal or colon cancer and for the diagnosis of same.

The conjugates and A/C hydro-dibenzoporphyrins of the present invention, labeled or unlabeled, can be administered systemically, in particular by injection, or can be used topically. The A/C hydro-dibenzoporphyrins or conjugates can be used singly or as components of mixtures.

Injection may be intravenous, subcutaneous, intramuscular, or, even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

For diagnosis, the compounds may be used alone or may be labeled with a radioisotope or other detecting means.

If the treatment is to be localized, such as for the treatment of superficial tumors or skin disorders, the active conjugates or A/C hydro-dibenzoporphyrins may be topically administered using standard topical compositions involving lotions, suspensions, or pastes.

The quantity of conjugate or A/C hydrodibenzoporphyrins derivative to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissue, such as those which comprise conjugates of the A/C and B/D hydro-dibenzoporphyrins with a highly specific monoclonal immunoglobulin preparation or specific receptor ligand, dosages in the range of 0.05–1 mg/kg are suggested. For compositions which are less specific to the target tissue, larger doses, up to 1–10 mg/kg may be needed. The foregoing ranges are merely suggestive, as the number of variables in regard to an individual treatment regime is large and considerable excursions from these recommended values are expected.

In addition to in vivo use, the compounds of the invention can be used in the treatment of materials in vitro to destroy harmful viruses or infectious agents. For example, blood plasma or blood which is to be used for transfusion or banked for future transfusion can be treated with the compounds of the invention and irradiated to effect sterilization. In addition, biological products such as Factor VIII which are prepared from biological fluids can be irradiated in the presence of the compounds of the invention to destroy contaminants.

EXAMPLES

The following examples are intended to illustrate the invention but not to limit its scope.

Preparation A

Preparation of Protoporphyrin II 7,17-Bis(methoxycarbonylethyl)-2,12 divinyl-3,8,13,18-tetramethyl-porphyrin (protoporphyrin II) was synthesized from acyclic precursors via dipyrromethene and a,c-biladiene intermediates, as described in "The Porphyrins" (supra) and in Scheme 1. The product was verified by UV, NMR and MS.

Preparation B

Preparation of A/C Dialkyl Analog 7,17-Diethyl-2,12-divinyl-3,8,13,18-tetramethylporphyrin was synthesized from acyclic precursors via dipyrromethene and a,c-biladiene intermediates as in Preparation A as shown in Scheme 2, and the product was verified by UV, NMR and MS.

EXAMPLE 1

Preparation of Disulfone A/C Hydro-dibenzoporphyrin

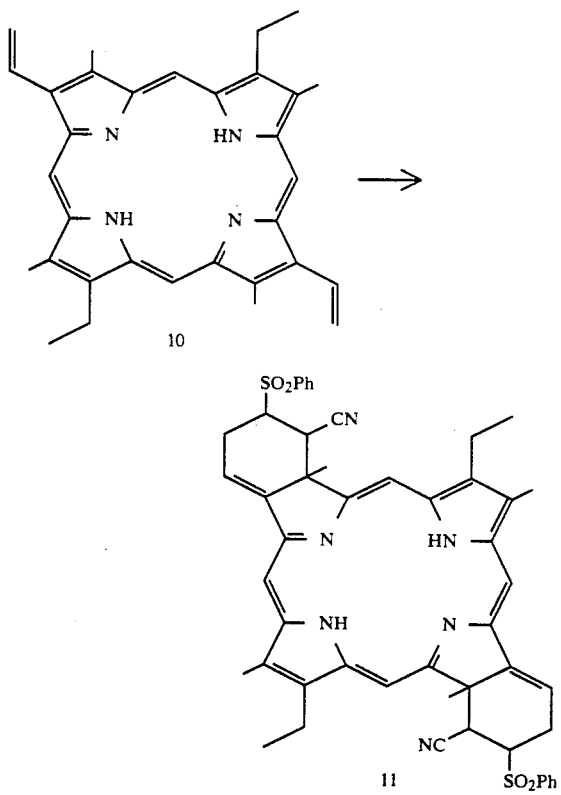

The protoporphyrin-II dialkyl analog (10) of preparation B (50 mg; 0.105 mmol) and (E)-b-phenylsulphonyl-acrylonitrile (1.01 g, 5.25 mmol) were dissolved/suspended in dry toluene (20 mL), degassed by three freeze-pump-thaw cycles and heated at 110° C. in a sealed tube for three days. The reaction mixture was evaporated to dryness in vacuo and the residue chromatographed on silica gel (activity I, 70-230 mesh, 100 g) using 2% methanol-dichloromethane as eluent. The fractions absorbing at 734 nm were combined, evaporated in vacuo and further purified using a chromatotron with a 1 mm silica gel plate. The title compound (11) was obtained as the major product (45% yield).

Figure 2A:
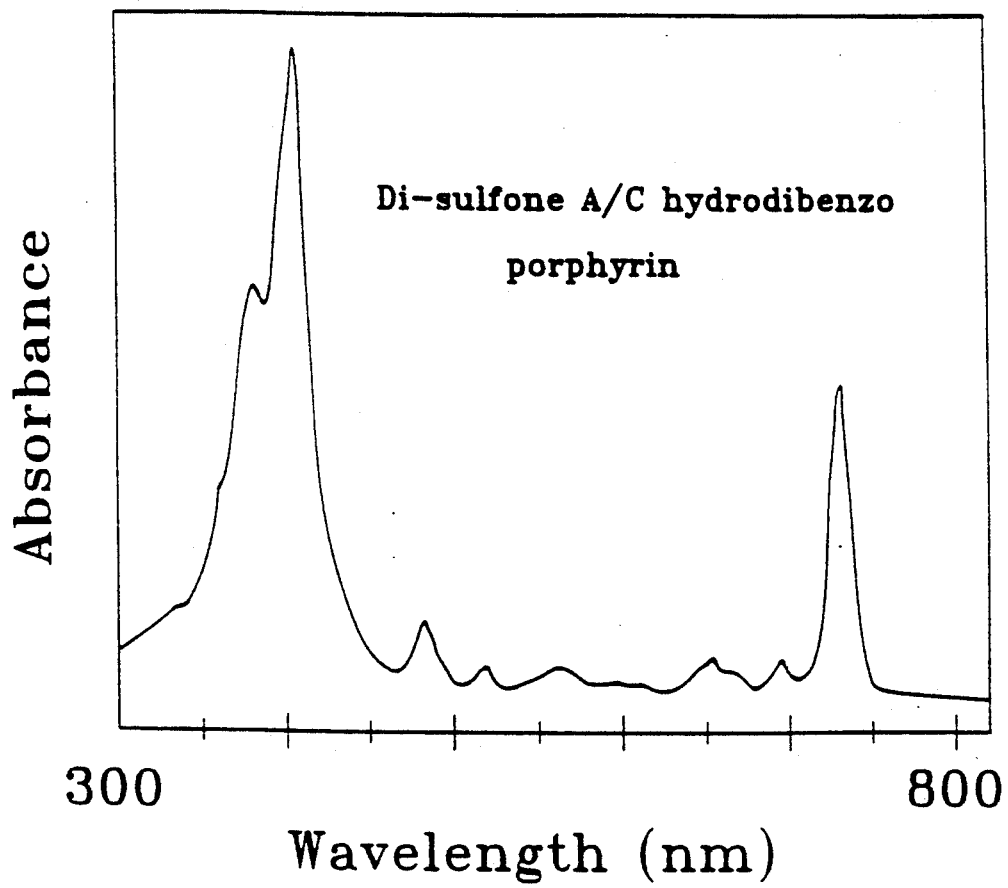
FIGS. 2A–2D show absorption spectra of several invention compounds.

UV$g_{max}$ (CH$_2$Cl$_2$) 384, 412 (Split Soret), 488, 520, 668, 698, 734 nm, shown in FIG. 2A.

$^1$H NMR (CDCl$_3$, 400 MHz): w −2.54 (s, 1H), −2.52 (s, 1H), 1.70 (t, 6H), 1.99, 2.01 (s, s, 6H), 2.01 (s, 3H), 3.36 (s, 6H), 3.25-3.60 (m, 4H), 3.75 (d, 2H), 3.78-3.86 (q, 4H), 4.31 (m, 2H), 7.00 (m, 2H), 7.50-8.05 (m, 10H), 9.05 (s, 2H), 9.33 (s, 2H).

FAB-MS m/a 861 (M+1).

EXAMPLE 2

Preparation of Dimaleamide A/C Hydro-dibenzoporphyrin

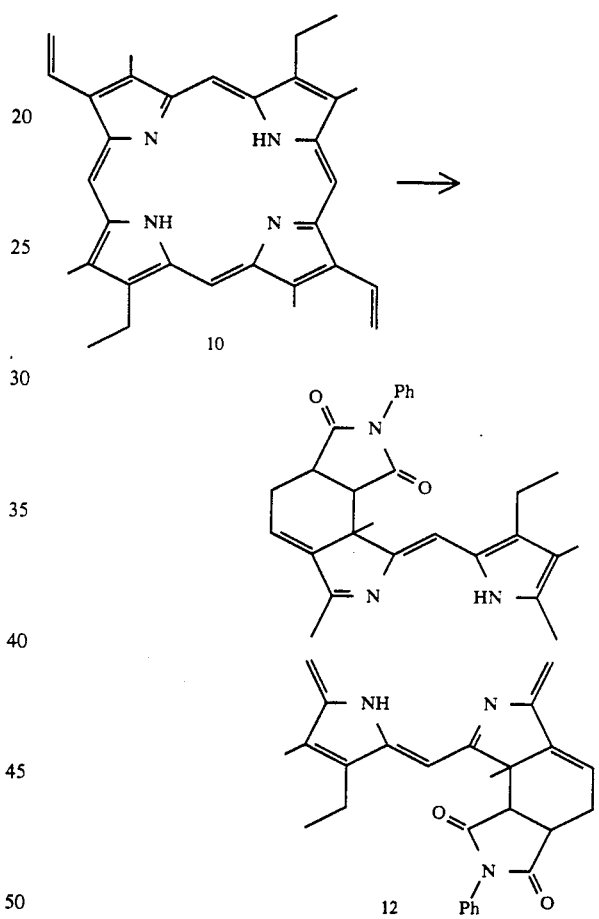

The protoporphyrin-II dialkyl analog (10) of preparation B (50 mg; 0.105 mmol) and N-phenylmaleimide 0.91 g (5.25 mmol) were reacted as described for the synthesis of title compound of Example 1. Purification by column chromatography (silica gel, 2% methanoldichloromethane) followed by further purification using the chromatotron (silica gel; 2% methanol-dichloromethane) afforded the A/C hydro-dibenzoporphyrin (12) as the major product (45%).

Figure 2B:
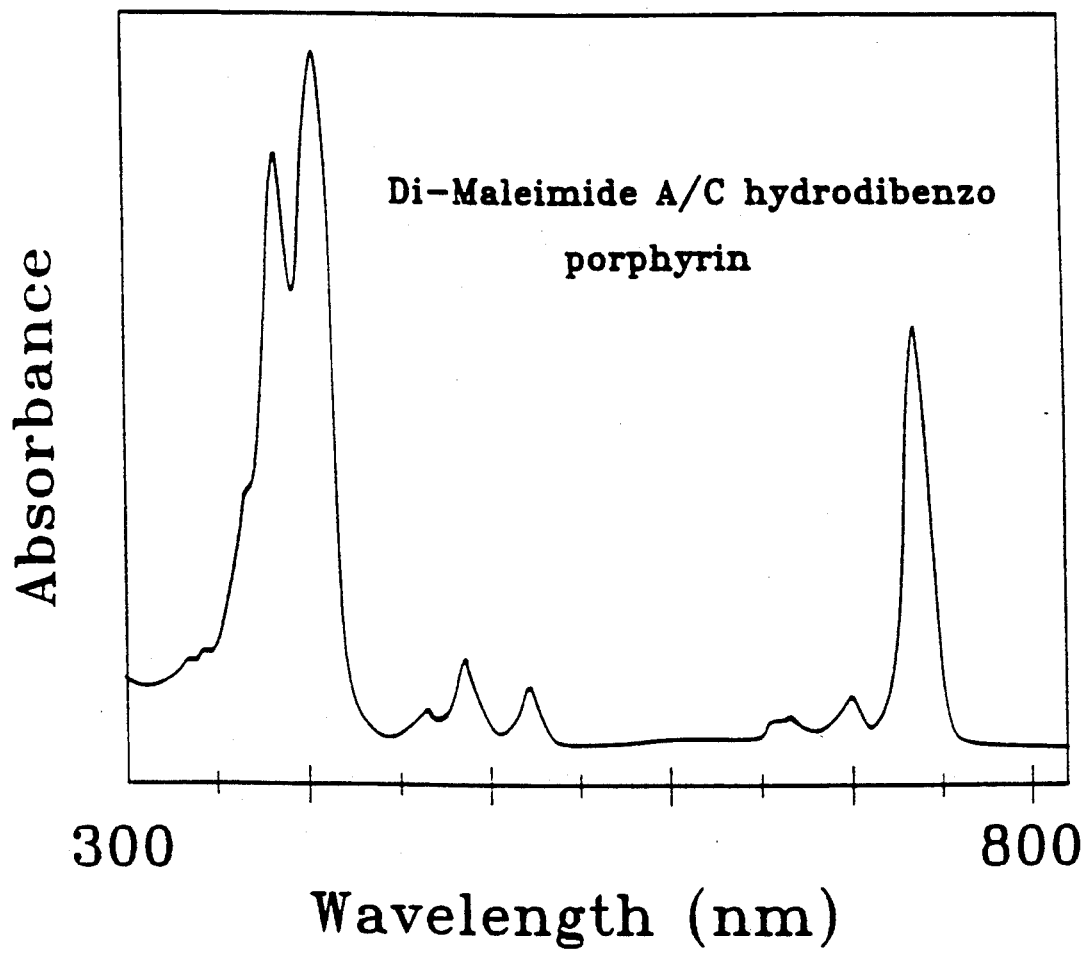

UV$g_{max}$ (CH$_2$Cl$_2$) 388, 410 (Split Soret), 490, 526, 702, 738 nm, shown in FIG. 2B.

$^1$H NMR (CDCl$_3$ 400 MHz): w −2.28 (s, 2H), 1.70 (t, 6H), 1.93, 2.02 (s, s, 6H), 3.35 (s, 6H), 3.40 (m, 4H), 3.82 (m, 2H), 3.85 (m, 4H), 4.55 (d, 2H), 6.60-7.0 (m, 10H), 7.22 (t, 2H), 8.90 (s, 2H), 9.05 (s, 2H).

MS m/e 820 (M+) 805, 647, 474.

EXAMPLE 3

Preparation of Tetracarbethoxy Hydro-dibenzoporphyrin

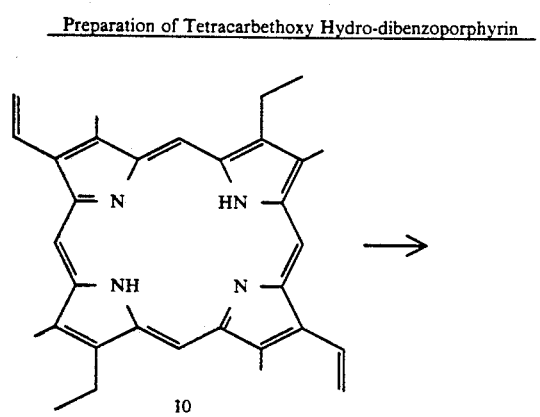

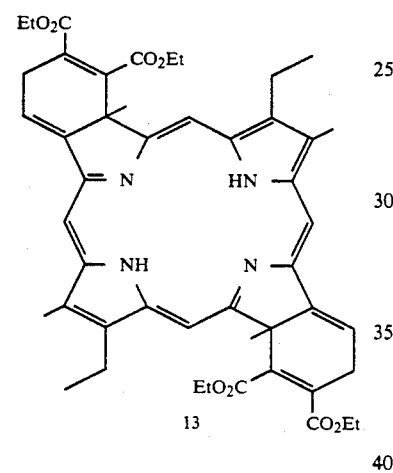

The protoporphyrin-II analog (10) of preparation B (50 mg; 0.105 mmol) and diethyl acetylene dicarboxylate (750 mg, 5.25 mmol) were reacted as described for the synthesis of compound 11. The excess dienophile was removed by flash chromatography on silica gel using $CH_2Cl_2$ as eluent. The major reaction products were eluted using 2% methanol-dichloromethane and rechromatographed using a chromatotron (silica gel; 2% methanol dichloromethane). The title compound (13) was obtained in 52% yield.

Figure 2C:
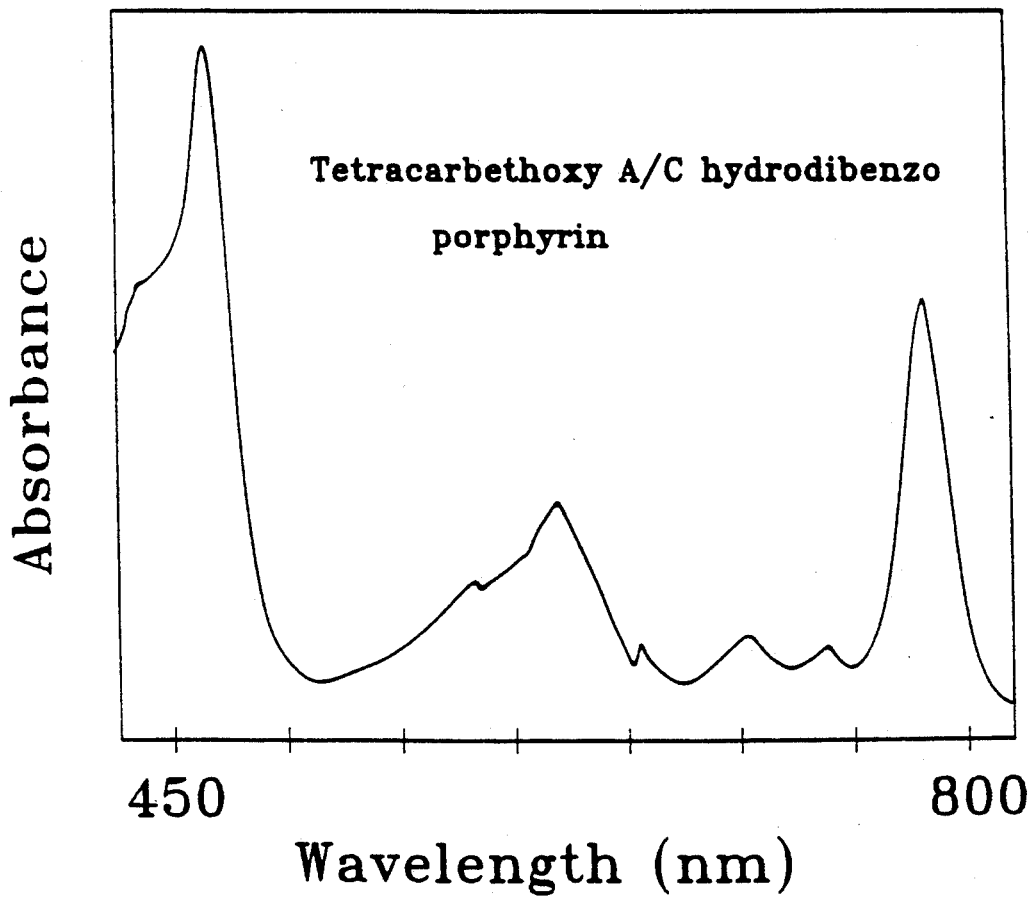

$UV_{gmax}$ ($CH_2Cl_2$) 38, 406 (split Soret), 484, 538, 698, 738 nm, shown in FIG. 2C.

$^1H$ NMR ($CDCl_3$, 400 MHz); w −2.51 (s, 2H), 1.08 (t, 6H), 1.40 (t, 6H), 2.00, 2.02 (s, s, 6H), 3.40 (s, 6H), 3.62 (m, 2H), 3.85 (m, 4H), 3.95 (m, 2H), 4.30–4.40 (m, 4H), 4.42–4.62 (m, 4H), 7.23–7.28 (m, 2H), 8.95 (s, 2H), 9.18 (s, 2H).

EXAMPLE 4

Rearrangement of Tetracarbethoxy A/C Hydro-dibenzoporphyrin

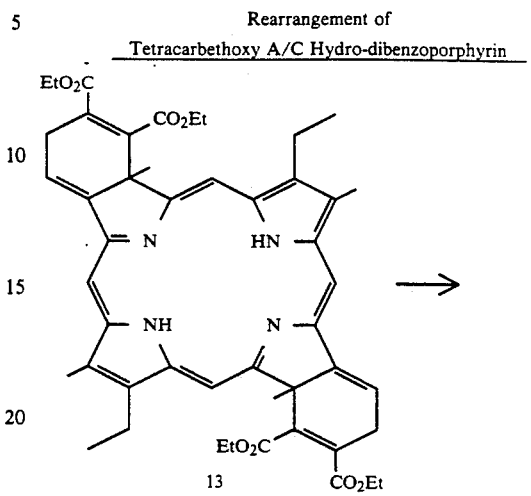

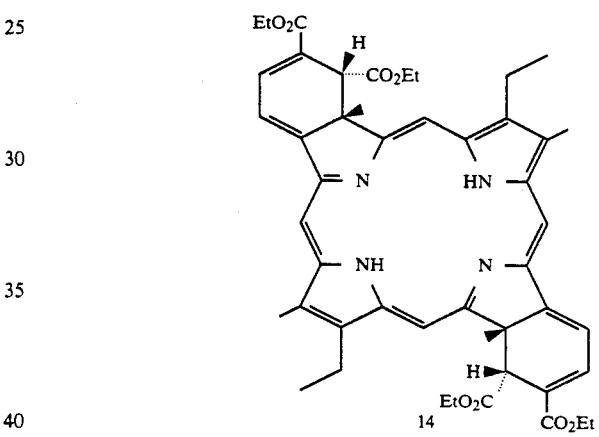

The A/C adduct of Example 3 (13) (20 mg, 0.025 mmol) was dissolved in freshly distilled dichloromethane (8 ml) and stirred in the dark with 1,8-diazabicyclo-[5.4.0]undec-7-ene (DBU). The reaction, monitored by visible spectroscopy, was complete in 3 h. The mixture was poured into 1M hydro chloric acid, extracted with dichloromethane, the organic layer washed with brine (twice) and water (once) and dried ($MgSO_4$). The product was purified by chromatography on silica gel using the chromatotron with 2% methanol-dichloromethane as the eluent; yield f90% of compound 14.

$UV_{gmax}$ ($CH_2Cl_2$) 448 (sh), 468 (Soret), 588 (sh), 622, 702, 742, 784 nm.

$^1H$ NMR ($CDCl_3$, 400 MHz); b −1.87 (s br. 2H), 0.33, 0.38 (t, 6H), 1.46 (t, 6H), 1.74, 1.78 (s, s, 6H), 1.75 (t, 6H), 3.30–3.60 (m, 4H), 3.35 (s, 6H), 3.75–3.90 (m, 4H), 4.35–4.50 (m, 4H), 4.90 (s, 2H), 7.28, 7.78 (2d, 4H) 8.76 (s, 2H), 9.13 (s, 2H).

MS m/e 814 (M+) 726, 638.

EXAMPLE 5

Preparation of an A/C
Tetracarbethoxy Hydro-dibenzoporphyrin and Its Rearranged and Hydrolyzed Products

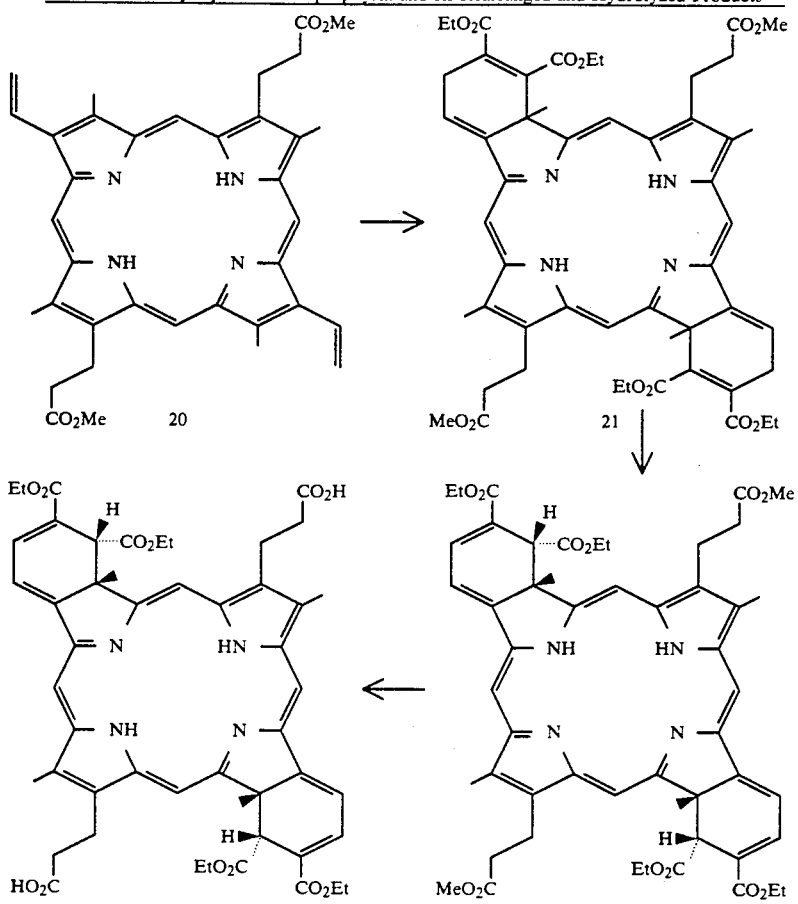

A. Protoporphyrin-II dimethyl ester (20) of preparation A (25 mg; $4.2 \times 10^{-5}$ mol) and diethyl acetylenedicarboxylate (620 mg; $4.2 \times 10^{-3}$ mol) were dissolved/-suspended in freshly distilled toluene (7 mL) and treated as described for the synthesis of the title compound of Example 1, compound 11. Excess reagent and unreacted starting material were removed by flash chromatography on silica gel and the mixture of products were eluted (1% ethanol-dichloromethane) and rechromatographed on silica gel using the chromatotron (2% methanol-dichloromethane). The A/C adduct of formula 21 was obtained in 30% yield.

UVg$_{max}$(CH$_2$Cl$_2$) 380, 406 (split Soret), 484, 516, 668, 700, 738 nm.

MS m/e 930 (M+).

B. The adduct prepared in paragraph A of this example was treated with 1,8 diazobicyclo(5.4.0]undec-7-ene (DBU) as described in the synthesis of the rearranged compound of Example 4. Following the usual work-up and purification, the rearranged product of formula 22 was obtained in near quantitative yield.

UVg$_{max}$(CH$_2$Cl$_2$) 446 (sh), 466 (Soret), 584 (sh), 616, 702, 744, 786 nm.

MS m/e 930 (M+).

C. The rearranged compound prepared in paragraph B was treated with 25% hydrochloric acid and allowed to stand for 5 h at room temperature in the dark. The reaction mixture was dried in a vacuum desiccator over KOH (overnight) and dissolved in dilute aqueous sodium hydroxide, to obtain the hydrolyzed dicarboxylic acid salt.

UVg$_{max}$ (H$_2$O; pH-10)406 (sh), 464 (Soret), 618, 708, 740 (wk) 790 nm.

The above solution was acidified with glacial acetic acid to obtain the compound of formula 23.

Figure 2D:
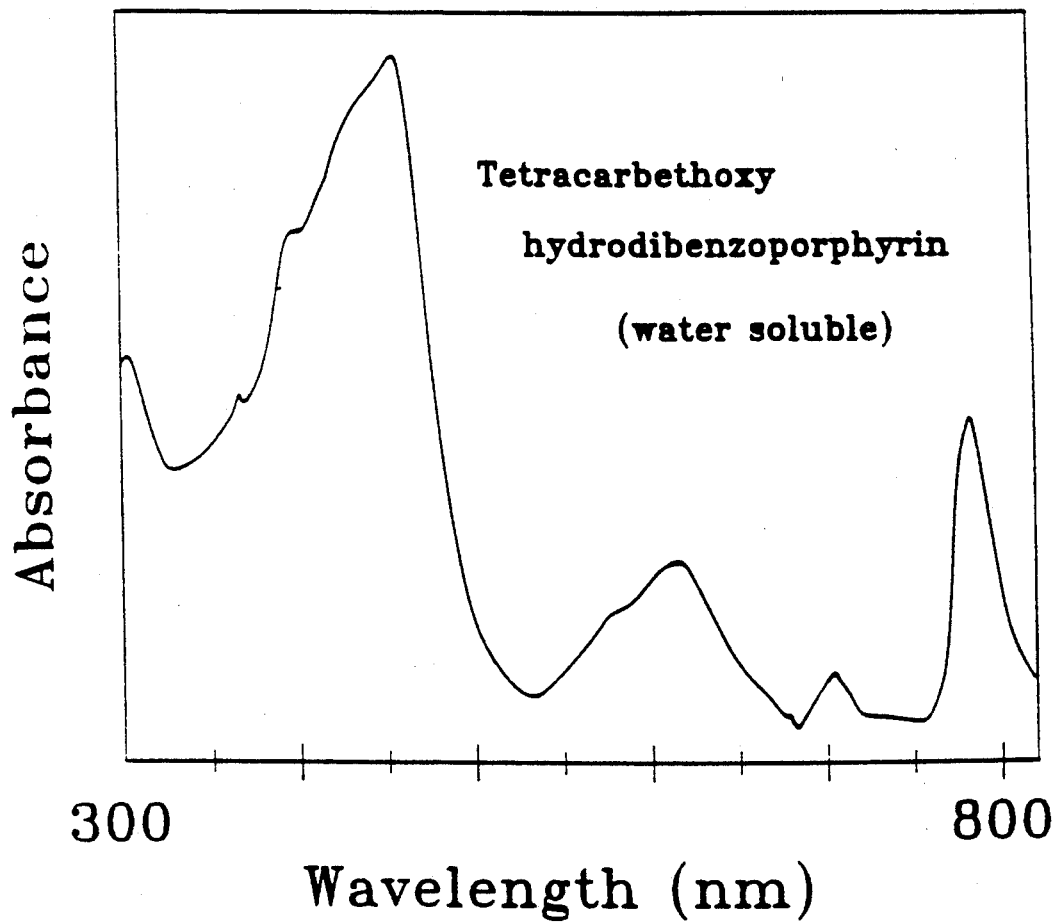

UVg $_{Max}$(H$_2$O; pH-3) 442 (Soret), 466 (Sh), 624, 708, 796 nm, as shown in FIG. 2D.

The product was extracted into ethyl acetate.

Uvg$_{max}$ (ethyl acetate) 444 (sh), 464 (Soret), 614, 698, 740, 782 nm.

EXAMPLE 6

Preparation of Immunoconiugates

This example describes methods of preparation for immunoconjugates of four different antibody preparations with either hematoporphyrin (Hp) or the invention hydro-dibenzoporphyrins. In this example, the invention compound 13 wherein R$^1$ and R$^2$ are carboethoxy, R$^3$=R$^3$ ethyl, and all R$^4$ are methyl is used. The antibodies employed are CAMAL-1, anti-M1 antibody, and B16G antibody, all prepared as described hereinabove, and affinity-purified rabbit/antimouse Ig (RaMIg).

One preparation of the conjugates is basically as described in Mew, D., et al., J Immunol (1983) 130:1473 (supra). Briefly, to 220 mg Hp.0.2 HCl (Sigma Chemical Co., St. Louis, Mo.) in 25 ml water and 0.8 ml N.N-dimethylformamide was added 20 mg 1-ethyl-3-(3- dimethylaminopropyl)-carbodiimide HCl (EDCI) in 0.6 ml water. After 30 minutes, this solution was mixed with 15 mg of the antibody protein dissolved in 5 ml distilled water and incubated for 5 hours. During this period, the pH of the solution was monitored and adjusted to between 6 and 7. Then 50 ml of monoethanolamine were added, and the solution allowed to stand overnight at room temperature. The solution was dialyzed against 0.001M phosphate buffer pH 7.4 for four days with three changes per day and overnight against PBS. The conjugate of the invention compound 13 is analogously prepared.

In a preferred method, the conjugation is conducted in an entirely nonaqueous solvent.

In a typical protocol, 2 ml of a dispersion in DMSO containing 5 mg each of the Hp or compound 13 and the dehydrating agent is prepared and stirred for 30 minutes at room temperature under nitrogen. To this is added a dispersion containing 2 mg of the appropriate immunoglobulin in 2 ml of DMSO, and the resulting mixture is stirred for another 10 minutes. This mixture is then worked up by dilution in phosphate-buffered saline, pH 7.4 (PBS), by adding 5 times the volume of PBS containing 50 ml monoethanolamine, and is then dialyzed against PBS using three changes of wash.

Alternatively, 2 ml of a dispersion containing 5 mg each of Hp or compound 13, a linking agent, and a dehydrating agent is prepared and stirred for approximately 15 minutes at room temperature under nitrogen. To this is then added a dispersion containing about 2 mg of the immunospecific protein in 2 ml of tetrahydrofuran and the resulting mixture stirred for another 10 minutes. The mixture is then worked up as described above.

The foregoing procedures are appropriate for CMAL-1 and for the remaining antibody preparations above listed.

In addition, the following preparations are made specifically with B16G and RaMIg:

B16G

Eleven Mg of hematoporphyrin plus 11 mg of EDCI in 4 ml spectral grade DMSO was stirred for 30 minutes under nitrogen at room temperature before the addition of 20 mg lyophilized B16G antibodies, prepared as described by Maier, T., et al., *J Immunol* (1983) 131:1843, in 2 ml DMSO. The resulting mixture was stirred for 40 seconds at room temperature and worked up as described above. The resulting product contained 375 mg Hp/mg B16G. A similar procedure is used substituting compound 13 for Hp.

RaMIg

Four hundred mg of EDCI and 400 mg hematoporphyrin in 1 ml DMSO were stirred for 30 minutes under nitrogen at room temperature as above before the addition of 800 mg lyophilized RaMIg antibodies, prepared as described by Mew, D., et al., *J immunol* (1983) 1473-1477, in 1 ml DMSO. The resulting mixture was stirred for 30 seconds and worked up as described above to obtain a product containing 200 mg Hp/mg RaMIg. A similar procedure is used substituting compound 13 for Hp.

EXAMPLE 7

Cytotoxicity of Hydro-dibenzo Porphyrins

Various invention compounds were assayed in vitro using either cell line P815 or MI-S as model systems to test their photosensitizing activity. In the standard protocol, various concentrations of test compounds were added to washed suspensions of cells from cultures of the target cells and the mixtures were then irradiated using 700-820 nm light for 30 minutes. The results were assayed by determining cytotoxicity using direct counting using eosin-Y exclusion, a standard procedure for differentiating living from dead cells.

In other determinations conducted as above, the cells recovered from light exposure were assayed for viability by incubating them for 18 hours in 10 mCi/ml tritium-labeled thymidine according to the standard procedure whereby thymidine incorporation is equated with viability. The cells were harvested and radioactivity uptake was measured by a scintillation counter. The results obtained are shown in Table 1 below; all $R^4$ are methyl; all compounds are of the formula 1-3.

TABLE 1

| | Compound | $LD_{50}$ | Cell Line |
|---|---|---|---|
| | BPD-MA (standard) | 8.0 ng | P815 |
| (11) | $R^1 = CN, R^2 = SO_2Ph, R^3 = R^3 = $ ethyl | 35 ng | P815 |
| (12) | $R^1-R^2 = -CONPhCO-, R^3 = R^3 = $ ethyl | F18 ng | P815 |
| (13) | $R^1 = R^3 = COOEt, R^3 = R^3 = $ ethyl | ND | P815 |
| | BPD-MA (standard) | 12.5 ng | MI-S |
| (11) | $R^1-CN, R^2 = SO_2Ph, R^3 = R^3 = $ ethyl | 300 ng | MI-S |
| (12) | $R^1-R^3 = -CONPhCO-, R^3 = R^3 = $ ethyl | 100 ng | MI-S |
| (13) | $R^1 = R^2, COOEt, R^3 = R^3 = $ ethyl | f1-2 ng | MI-S |

We claim:

1. A method to detect, photosensitize, destroy or impair the functioning of target biological material, which comprises:

a. contacting said target with an effective amount of a composition having a light absorption maximum between 700-820 nm, and b. irradiating said target with light that excites said composition;

wherein the composition comprises a compound selected from the group consisting of the structures 1-1 through 1-6 shown below or mixtures thereof,

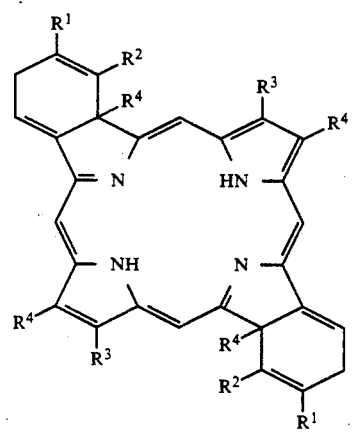

1-1

-continued

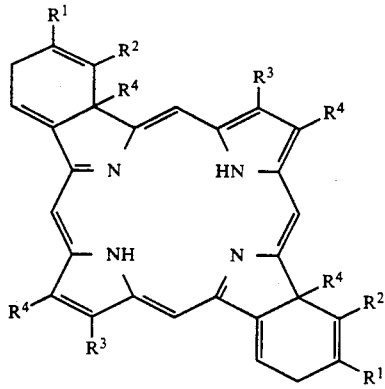

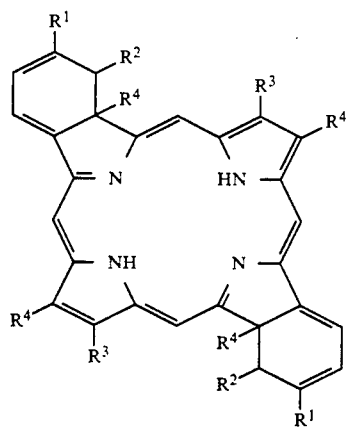

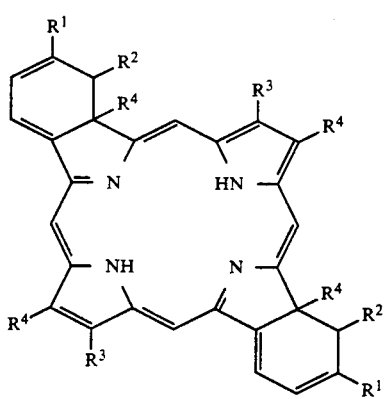

-continued

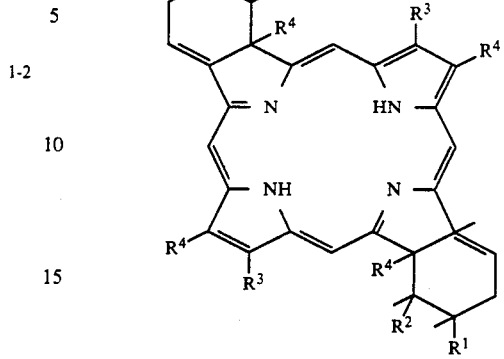

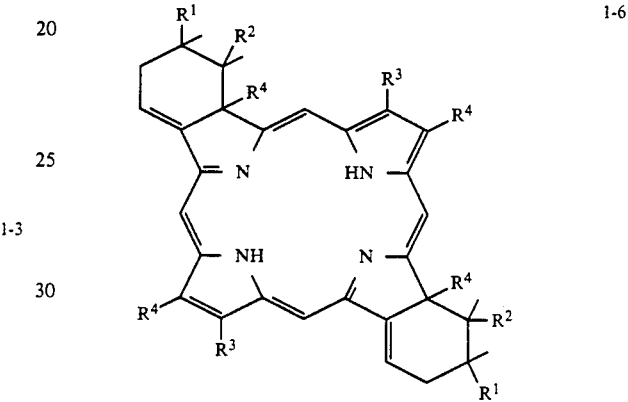

wherein at least one of $R^1$ and $R^2$ is selected from the group consisting of carbalkoxy (2-6C); aryl (6-10C); alkyl (1-6C) or aryl (6-10C) sulfonyl; cyano; and —$CONR^5CO$—, wherein $R^5$ is aryl (6-10C) or alkyl (1-6C);

the other $R^1$ and $R^2$ is selected from the group consisting of the aforesaid substituents and H; and each $R^3$ and $R^4$ is independently selected from the group consisting of substituted or unsubstituted alkyl (1-6C); and substituted or unsubstituted omega-carboxyalkyl (2-6C) and the esters, amides, and salts thereof.

2. A method to detect or impair the metabolism of or to effect the destruction of target virus, cells, or tissues which comprises contacting said target with an effective amount of the compound of claim 1, or a pharmaceutical composition thereof, and irradiating the contacted virus, cells, or tissues with light which excites said composition.

3. A method to detect a target virus, cell or tissue in vivo, which comprises:
   a. administering to a subject harboring said target an effective amount of a composition having a light absorption maximum between 700–820 nm, wherein the composition comprises the compound of claim 6;
   b. irradiating said target with light that excites said composition; and
   c. detecting the location of said composition.

4. The method of claim 3 wherein the composition further contains a label.

* * * * *